United States Patent [19]
Gilman

[11] Patent Number: 6,086,912
[45] Date of Patent: Jul. 11, 2000

[54] TOPICAL DRUG DELIVERY SYSTEM

[76] Inventor: Marvin S. Gilman, 17 Woodbrook Cir., Wilmington, Del. 19810

[21] Appl. No.: 09/022,335

[22] Filed: Feb. 11, 1998

[51] Int. Cl.[7] .............................. A61F 13/02; A61F 13/00
[52] U.S. Cl. ........................ 424/449; 424/448; 424/449
[58] Field of Search ..................... 424/448, 449

[56] References Cited

U.S. PATENT DOCUMENTS

| | | | |
|---|---|---|---|
| 1,212,731 | 1/1917 | Banks | 602/78 |
| 4,366,814 | 1/1983 | Riedel | 128/156 |
| 4,435,180 | 3/1984 | Leeper | 604/896 |
| 4,842,931 | 6/1989 | Zook | 428/354 |
| 5,098,421 | 3/1992 | Zook | 604/367 |
| 5,167,649 | 12/1992 | Zook | 604/307 |
| 5,181,914 | 1/1993 | Zook | 604/307 |
| 5,267,952 | 12/1993 | Gardner | 602/58 |
| 5,415,866 | 5/1995 | Zook | 424/448 |
| 5,538,500 | 7/1996 | Peterson | 602/48 |
| 5,662,925 | 9/1997 | Ebert | 424/447 |

*Primary Examiner*—Thurman K. Page
*Assistant Examiner*—Susan Tran
*Attorney, Agent, or Firm*—Herbert M. Wolfson

[57] ABSTRACT

A drug delivery system for the topical administration of medication or other therapeutic material wherein the prior art peripheral layer of adhesive surrounding the active drug delivery area of the system is replaced by a bandage wrap.

2 Claims, 2 Drawing Sheets

TOPICAL DRUG DELIVERY SYSTEM

FIELD OF THE INVENTION

This invention relates to drug delivery systems for the topical administration of medication, therapeutic material or the like into the body by affixing a patch containing the medication or the like in firm contact with the patient's skin.

BACKGROUND OF THE INVENTION

In the delivery of physiologic amounts of testosterone to produce circulating concentrations approximating the normal circadian rhythm of healthy men, a system shown schematically in FIG. 1 is used. Proceeding from the top of the Figure toward the surface in contact with the patient's skin, the system is composed of 11 a transparent ethylene-vinyl acetate copolymer/polyester laminate as a backing film; 12 a drug reservoir of testosterone, alcohol, glycerin, glycerol monoaleate and methyl laurate gelled with an inert acrylic acid copolymer, 13 a permeable polyethylene microporous membrane; and 14 a peripheral layer of an adhesive surrounding the central, active drug delivery area of the system.

Prior to opening the system and applying the system to the skin, the central delivery system 12 is sealed with a peelable disc 15. The disc is composed of a five-layer laminate including a layer of aluminum foil which give the disc a silver appearance. The "silver" disc 15 is attached to, and removable with the release liner 16, a silicone-coated polyester film.

To use, the tabs 17a and 17b, extending from the patch 14 and the release liner 16, respectively, are gently pulled apart as shown in FIG. 2, to remove the liner 16 and the silver disc 15. This operation will expose the adhesive layer 14 and the central reservoir area 12 covered by the microporous membrane 13. The resulting patch is then applied to the skin by pressing the adhesive layer 14 firmly against the skin.

Such systems have been used successfully for many years for topical administration of many medicinal and therapeutic materials. However, in recent years the use of such systems, particularly with heart patients who must consume relatively high dosages of blood-thinning medication, has produced bleeding problems. The simple explanation lies in the adhesive layers used in the delivery systems. When the patches that are firmly adhered to the patient's skin are removed, the thin skin of the heart patient tends to be removed as well, resulting in immediate bleeding.

The object of the present invention is to overcome this dangerous problem.

Specifically, the object of the present invention is to provide a drug delivery system for the topical administration of therapeutic or medicinal material without contacting the patient's skin with an adhesive and without losing any of the efficiency of the drug delivery system.

Other objects will appear hereinafter.

SUMMARY OF THE INVENTION

The objects are accomplished by wrapping an elastic bandage material around the patient's body part to press the drug delivery system against the skin of the patient and omitting the detrimental adhesive layer.

Specifically, the invented article comprises a length of elastic bandage material, adapted to encircle the patient's body part, e.g., arm, leg, thigh, etc.; a length of backing film, the outer surface of which is in contact with the bandage material, preferably attached to the bandage material. The film is sufficiently limp and pliable to enable a reservoir to form for the medication to be applied, the medication being within the reservoir and in contact with the inner surface of the backing film. A permeable microporous membrane is disposed over the complete area of the reservoir to contain the medication within the reservoir; and a disc composed of several layers including at least one opaque layer, preferably a reflective layer such as aluminum foil, to seal the reservoir, and disposed tightly over the microporous layer. Finally, a release liner which may be composed of a silicone-coated polyester film, is attached to and over the opaque disc.

DETAILED DESCRIPTION OF THE INVENTION

The elastic bandage material used in the drug delivery system of this invention may be any of the tapes and fabrics described in U.S. Pat. No. 4,366,814, whose disclosure is incorporated herein by reference. The material, as used in the present invention should exhibit a degree of stretchiness and porosity that is insufficient to unduly restrict the movement or the "breathability" of the underlying skin.

The material may also contain a small amount of adhesive on only one surface to prevent the wrapping layers of material from slipping and, thus, loosening the wrap to the extent that the microporous membrane, through which the medication flows into the patient loses contact with the patient's body part. Such elastic material is available as COBAN®, a registered trademark of the Minnesota Mining and Manufacturing Company.

However, it should be understood that non-treated fabric, preferably elastic material as described in U.S. Pat. No. 4,366,814 without any adhesive on the surface, may also be used. Such material may be used with a single wrapping layer over the delivery system layer shown in FIG. 3 and secured by means of a fastener which may be a slotted clamp as shown in U.S. Pat. No. 1,212,731, a safely pin, a hook-and-loop fastener, i.e., "VELCRO", the fastener usually provided with "Ace" bandages, i.e., a flat rectangular metal piece having saw-tooth projections at each end to be inserted into the overlapping layers of the bandage material at the end of the top layer and into the underlayer where it is exposed beneath the top layer.

Figure 1:
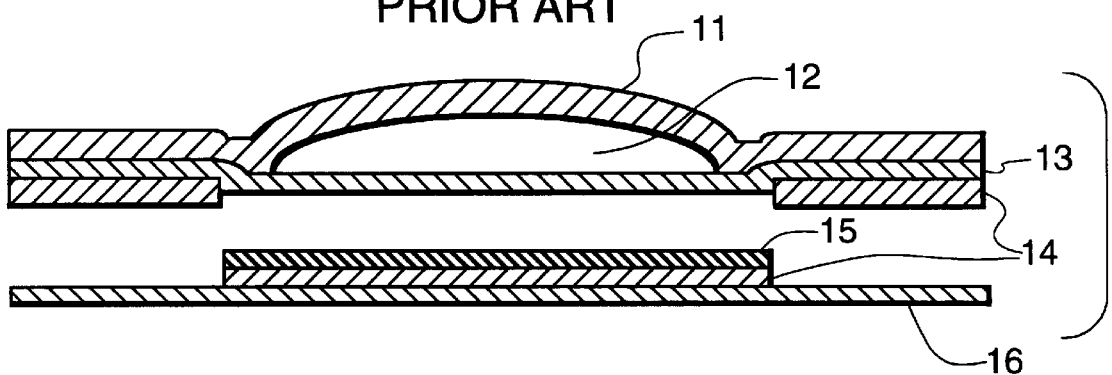
FIG. 1 is a cross-sectional side-view of the drug delivery system of the prior art.
Figure 2:
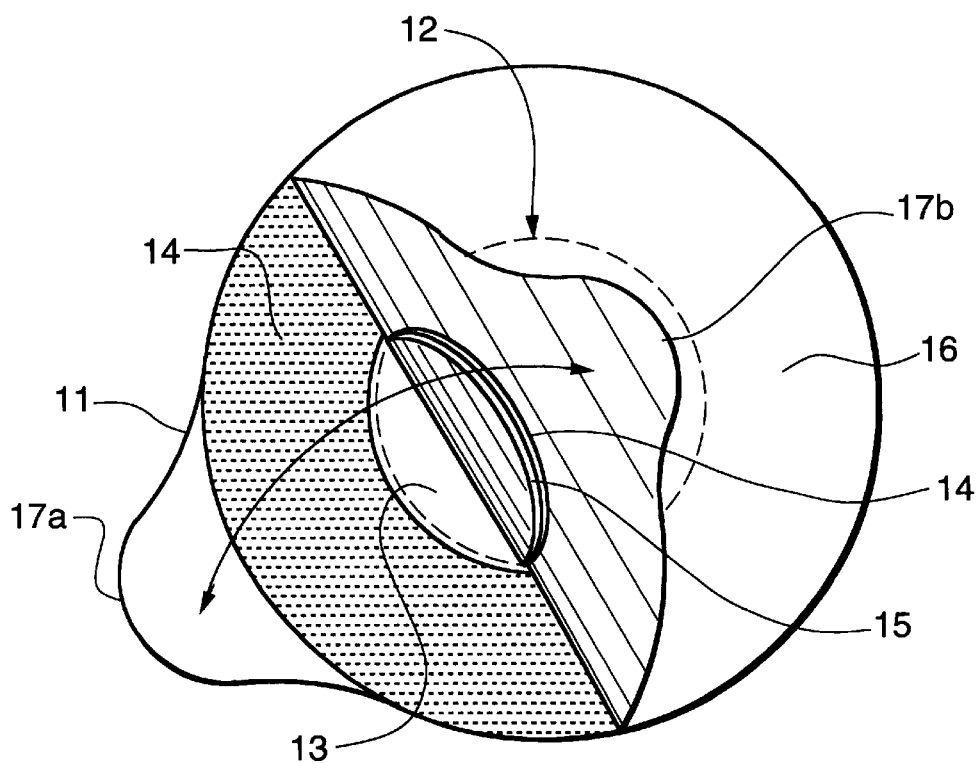
FIG. 2 is a view, in perspective, of removing the liner and disc from the system shown in FIG. 1.

Referring now to the drawings, there is shown in FIGS. 1 and 2 a cross-sectional view of the drug delivery system of the system and the manner in which the system is prepared to be affixed to the patient's skin by exposing the porous membrane through which the medication will flow and exposing the adhesive layer which will be placed in adhesive contact with the patient's skin. The procedure is discussed in detail in the Background section of this specification.

Figure 3:
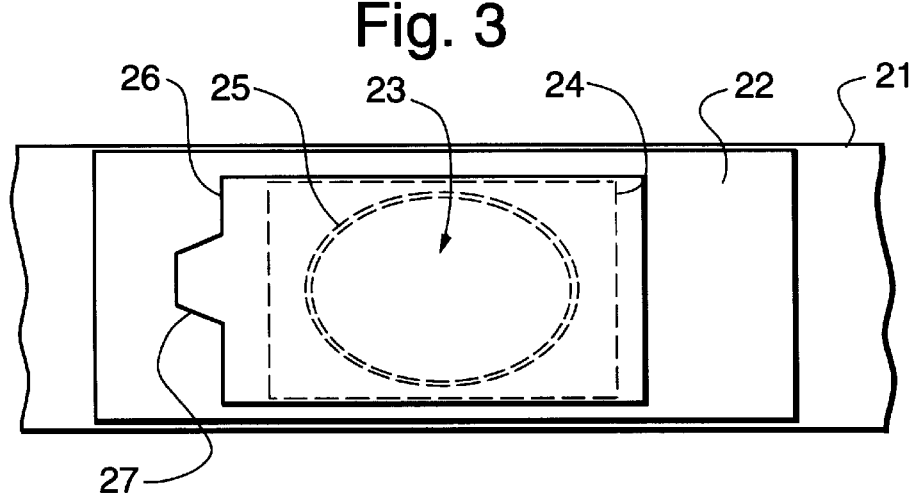
FIG. 3 is a plan view of a preferred embodiment of the drug delivery system for the topical administration of medication.
Figure 4:
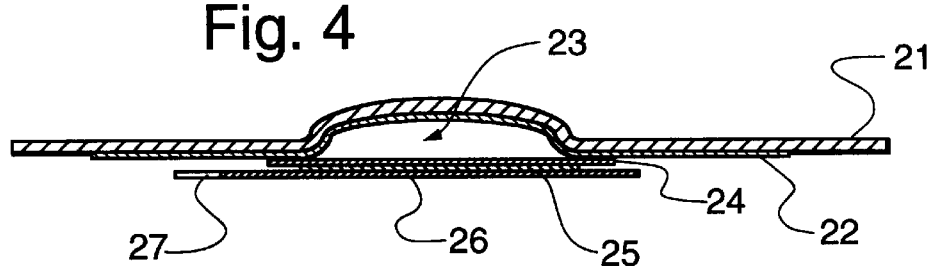
FIG. 4 is a cross-sectional side view of the drug delivery system of the invention.
Figure 5:
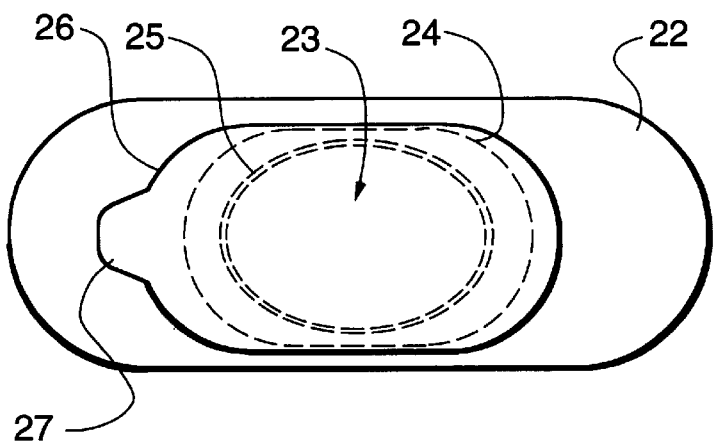
FIG. 5 is a plan view of the drug delivery system without the elastic wrapping material.

FIGS. 3 and 4 represent the preferred embodiment of the topical drug delivery system of this invention. Proceeding from the top in FIG. 4, the system is composed of the bandage material 21, which preferably comprises at least 50% of an extensible porous fabric capable of at least 30% elongation in one direction without tearing and about 15% of an elastomer uniformly impregnated in the fabric without affecting the oxygen or moisture vapor permeabilities of the fabric or the non-adherability of the fabric to the skin of the patient. The length of the bandage material 21 is sufficient to provide at least one layer to wrap over the layer containing the medication reservoir 23.

Attached or adhered to the under surface of the bandage material is a length of a thin backing film 22, preferably a transparent ethylene/vinyl acetate copolymeric film laminated to polyester film. The film is sufficiently limp to permit the formation of an elliptical groove or reservoir 23, about 2 inches long and 1¼ inches wide. Over the groove 23 and attached to the backing film 22 around the periphery is a permeable polyethylene microporous membrane 24 which covers and contains the medication in groove 23. Extending over the membrane 24 is a peelable disc 25 having dimensions substantially the same as those of the membrane 24. The disc is composed of the five-layer laminate described previously. Over the disc 25 is the release liner 26, about 3¼ inches×2⅜ inches. Liner 26 is adhered to disc 25 and peelably attached to the backing film 22.

To use the system, the release liner 26 is gently pulled by the tab 27 from the backing film 22 to remove the disc 25 (adhered to liner 27) and to expose the membrane 24. The elastic bandage material 21 is then wrapped around the patient's body part with the membrane 24 in firm contact with the skin area in which the medication from reservoir 23 is to be delivered.

What is claimed is:

1. A method for delivering a drug through the skin of a patient without contacting the skin which an adhesive consisting essentially of:

a. attaching a pliable first layer to the surface of a length of stretchable material;

b. placing medication on a limited area of said first layer;

c. attaching a permeable microporous layer to said pliable layer in such manner as to form a groove as a reservoir for containing said medication in said first layer;

d. placing a sealing material comprised of at least one impermeable layer over said microporous layer covering said groove to seal said reservoir;

e. removing said sealing material immediately prior to wrapping said stretchable material at least once around a patient's body part;

f. and releasing said medication from said reservoir to the patient's skin.

2. A system to deliver medication through a patient's skin without contacting the patient's skin with an adhesive consisting essentially of:

a. a stretchable material of sufficient length to be wrapped at least once around a patient's body part and to provide a second winding adapted to overlap and secure itself to the first winding;

b. a pliable first layer attached to a surface of said stretchable material;

c. a permeable microporous layer attached to said pliable first layer and adapted to form a groove in said layer;

d. therapeutic or medicating material distributed in said groove;

e. impermeable material of sufficient toughness shaped to cover said membrane and to seal said medicating material in said groove;

f. a second layer disposed over and firmly attached to said impermeable cover and peelably attached to said pliable first layer whereby, when said second layer is peeled from said first layer, said medication is delivered through the patient's skin.

* * * * *